United States Patent [19]
Böckmann et al.

[11] Patent Number: 4,528,146
[45] Date of Patent: Jul. 9, 1985

[54] PROCESS FOR THE PREPARATION OF TEREPHTHALOYL AND ISOPHTHALOYL DICHLORIDES

[75] Inventors: Walter Böckmann; Friedrich Brühne; Karl-August Lipper, all of Krefeld, Fed. Rep. of Germany

[73] Assignee: Bayer Aktiengesellschaft, Leverkusen, Fed. Rep. of Germany

[21] Appl. No.: 493,905

[22] Filed: May 12, 1983

[30] Foreign Application Priority Data

Jun. 2, 1982 [DE] Fed. Rep. of Germany ....... 3220729

[51] Int. Cl.$^3$ .............................................. C07C 51/60
[52] U.S. Cl. .................................. 260/544 D; 260/694
[58] Field of Search ..................................... 260/544 D

[56] References Cited
U.S. PATENT DOCUMENTS 2,676,187  4/1954  Foster et al. .................... 260/544 D
2,865,959  12/1958  Toland ............................ 260/544 D
3,878,244  4/1975  Zengel et al. .................. 260/544 D

OTHER PUBLICATIONS

*The Condensed Chemical Dictionary,* Van Nostrand, Publ. (1974), pp. 316, 485, 851 and 852.

Primary Examiner—Natalie Trousof
Assistant Examiner—L. Hendriksen
Attorney, Agent, or Firm—Sprung, Horn, Kramer & Woods

[57] ABSTRACT

An improved process for the preparation of terephthaloyl and isophthaloyl dichlorides by chlorination of dimethyl terephthalate and isophthalate with chlorine gas at temperatures from 100°–250° C., optionally in the presence of light and/or catalysts promoting side-chain chlorination of aromatic compounds, according to which 20 to 200% by weight, relative to the weight of dimethyl terephthalate and/or isophthalate, of terephthaloyl and/or isophthaloyl dichloride are added to the dimethyl terephthalate and/or isophthalate for the chlorination.

12 Claims, No Drawings

PROCESS FOR THE PREPARATION OF TEREPHTHALOYL AND ISOPHTHALOYL DICHLORIDES

The invention relates to an improved process for the preparation of terephthaloyl and isophthaloyl dichlorides by chlorination of dimethyl terephthalate and isophthalate.

The preparation of aromatic monocarbonyl and polycarbonyl chlorides by chlorination of the corresponding methyl esters at elevated temperatures and optionally in the presence of light or catalysts promoting side-chain chlorination of aromatic compounds is known. Thus, in German Pat. No. 1,064,495, a process for the preparation of chlorides of aromatic monocarboxylic and polycarboxylic acids is described, according to which the corresponding methyl esters are chlorinated with chlorine in the presence of light at temperatures from 100° to 220° C. preferably 150° to 180° C. According to U.S. Pat. No. 2,865,959, aromatic acid chlorides are prepared by the action of chlorine gas on alkyl esters of aromatic carboxylic acids at temperatures from 149° to 371° C. (300° to 700° F.), preferably up to 316° C. (600° F.) in the presence or in the absence of catalysts, such as light, iron(III) chloride, antimony(III) chloride, cerium(III) chloride and zinc chloride.

However, difficulties occur in using this process for the preparation of terephthaloyl and isophthaloyl dichlorides, since a sublimate forms on chlorination of dimethyl terephthalate and isophthalate, and this easily leads to blockage of the effluent gas lines and consequently to a dangerous rise in pressure in the reaction vessel.

It is proposed, in German Auslegeschrift No. 1,152,400, to prevent this interfering formation of the sublimate by carrying out the chlorination of dimethyl terephthalate and isophthalate in the presence of 2 to 10% by weight of liquid chlorides and methyl esters of aromatic monocarboxylic acids, the boiling points of which are in the region of the reaction temperature. However, this process has the disadvantage that working up the reaction mixture becomes industrially very elaborate due to the presence of the monocarbonyl chlorides which prevent the formation of a sublimate and which must be separated from the terephthaloyl and/or isophthaloyl dichloride to be isolated. Terephthaloyl and isophthaloyl dichloride are used for the preparation of high molecular weight polycondensates, for example aromatic polyamides and aromatic polyesters; during the further processing of these even extremely small amounts of monocarbonyl chlorides interfere, since they act as chain breakers. Even the smallest amounts of impurities in isophthaloyl and terephthaloyl dichloride cause a crucial diminution in the quality of the aromatic polyamides and polyesters prepared from them. For this reason, extremely strict requirements are made of the purity of terephthaloyl and isophthaloyl dichlorides.

It has now been found that the disadvantages of the known processes for the preparation of terephthaloyl and isophthaloyl dichlorides by chlorination of the corresponding dimethyl esters can be avoided by adding 20 to 200% by weight, relative to the weight of the dimethyl phthalate to be chlorinated, of terephthaloyl and/or isophthaloyl dichloride to the dimethyl terephthalate and/or isophthalate for the chlorination. By this measure, on the one hand, the interfering formation of a sublimate is prevented and, on the other hand, a chlorination product is obtained from which terephthaloyl and isophthaloyl dichloride can be isolated, in high yields and in a high purity hitherto not achieved, by fractional distillation without special industrial elaboration.

Thus the invention relates to a process for the preparation of terephthaloyl and isophthaloyl dichlorides by chlorination of dimethyl terephthalate and isophthalate with chlorine gas at temperatures from 100° to 250° C., optionally in the presence of light and/or catalysts promoting a side-chain chlorination of aromatic compounds, which is characterized in that 20 to 200% by weight, relative to the weight of the dimethyl terephthalate and/or isophthalate to be chlorinated, of terephthaloyl and/or isophthaloyl dichloride are added to the dimethyl terephthalate and/or isophthalate for the chlorination.

Terephthaloyl and/or isophthaloyl dichloride are preferably added to the dimethyl terephthalate and/or isophthalate to be chlorinated in an amount from 30 to 100% by weight relative to the weight of the dimethyl terephthalate and/or isophthalate to be chlorinated.

The isolation of the terephthaloyl and/or isophthaloyl dichloride from the reaction mixture obtained in the process according to the invention takes place in a conventional manner by fractional distillation.

It is true that, in Example 1 of German Auslegeschrift No. 1,152,400, a recycling of first runnings which in addition to benzoyl chloride will contain terephthaloyl dichloride is described, but the amount of terephthaloyl dichloride in these first runnings is too low to prevent the interfering formation of a sublimate.

In a preferred embodiment of the process according to the invention, the chlorination of dimethyl terephthalate and isophthalate carried out in the presence of terephthaloyl and/or isophthaloyl dichloride is discontinued as soon as the content of terephthaloyl and/or isophthaloyl dichloride in the reaction mixture has risen to 90 to 98% by weight. By this measure, excess chlorination with formation of nuclear chlorination and chlorolysis products is avoided. These undesired by-products can only be incompletely separated from terephthaloyl and/or isophthaloyl dichloride using distillation of normal elaboration, and they lead to an adverse effect on the quality of the terephthaloyl and isophthaloyl dichloride. It has been found, surprisingly, that, on distillation of the reaction mixture, the intermediate products still present in the reaction mixture from the incomplete chlorination mostly decompose with formation of the desired dichlorides or remain as partially chlorinated products in the tailings of the distillation. Since, as a rule, these tailings also contain relatively large amounts of terephthaloyl and/or isophthaloyl dichloride, they are used again in the next chlorination batch. That is to say, the terephthaloyl and/or isophthaloyl dichloride to be used according to the invention can be added to the dimethyl terephthalate and/or isophthalate to be chlorinated in the form both of the pure compounds or of mixtures of the pure compounds and in the form of these fractions from the preparation of terephthaloyl and/or isophthaloyl dichloride which contain these chlorides.

The chlorination according to the invention of dimethyl terephthalate and/or isophthalate is carried out at temperatures from 100° to 250° C., preferably from 150° to 200° C. The chlorination can be undertaken in the presence of light, for example light rich in UV radiation, and/or in the presence of radical-forming agents which promote the side-chain chlorination of aromatic compounds, such as azodiisobutyronitrile.

The process according to the invention can be carried out in the absence or in the presence of organic solvents which are inert under the reaction conditions. Examples of suitable inert organic solvents are halogenated hydrocarbons, such as hexachlorobutadiene. The chlorination can be carried out either discontinuously or continuously, for example in a cascade of 2 to 10 reactors. The starting compounds dimethyl terephthalate and isophthalate can be used either alone or as a mixture. If desired the chlorine gas used can be diluted with inert gases, such as nitrogen.

The process according to the invention has significant advantages compared to the known processes for the preparation of terephthaloyl and isophthaloyl dichlorides: the acid chlorides are obtained in high yields and higher degrees of purity than could hitherto be achieved, and the interfering formation of a sublimate, and with it the danger of blockage of the effluent gas lines, is avoided.

Terephthaloyl and isophthaloyl dichlorides are important intermediate products for the preparation of aromatic polyesters and polyamides.

EXAMPLE 1

A cylindrical chlorination vessel provided with a thermometer, reflux condenser, gas introduction tube (frit) and a light source (superactinic 20 watt fluorescent tubes) located in the middle of the vessel is charged with 777 g (4 mols) of dimethyl terephthalate and 406 g of terephthaloyl dichloride. The contents of the vessel are heated to 150° C. Dry chlorine gas is then passed in, while irradiating with light, at a rate of 50 liter/h in the first 6 hours and subsequently, appropriate for the diminished uptake, at a lower rate. A total of 1310 g of chlorine are passed in within 10 hours. No interfering formation of a sublimate occurs during the chlorination.

After completion of chlorination, the reaction mixture is freed of dissolved chlorine and other dissolved gases by blowing in nitrogen. The reaction mixture is subsequently distilled under reduced pressure (12.0 to 13.3 mbar). 1194 g of colourless terephthaloyl dichloride are obtained; boiling point 131°-134° C.; melting point 82° C.; degree of purity 99.9%.

Yield: 97.0% of theory.

If the chlorination is undertaken in the absence of terephthaloyl dichloride under conditions which are otherwise identical, the formation of a heavy sublimate occurs during chlorination.

The corresponding chlorination of dimethyl terephthalate in the presence of 5% benzoyl chloride in accordance with German Auslegeschrift No. 1,152,400 in place of the addition of terephthaloyl dichloride gives, after distillation, terephthaloyl dichloride with a degree of purity of 99.7% as the main run. 0.13% of benzoyl chloride is detectable among the impurities.

EXAMPLE 2

971 g (5 mols) of dimethyl isophthalate and 406 g of isophthaloyl dichloride are initially introduced into the apparatus described in Example 1, merely omitting the light source. Dry chlorine is passed in, at 200° C., initially at a rate of 50 liters/h and then, after 8 hours, at a lower rate appropriate for the diminished uptake. A total of 1710 g of chlorine is taken up within 13 hours. No interfering formation of a sublimate occurs during the chlorination.

After completion of chlorination, the reaction mixture is freed of dissolved chlorine and other dissolved gases by blowing in nitrogen and subsequently distilled under reduced pressure (12 to 13.3 mbar). 1385 g of colourless isophthaloyl dichloride are obtained. Boiling point 134°-137° C.; melting point 43° C.; degree of purity 99.9%.

Yield: 96.4% of theory.

EXAMPLE 3

388 g (2 mols) of dimethyl terephthalate, 388 g (2 mols) of dimethyl isophthalate, 203 g of terephthaloyl dichloride and 203 g of isophthaloyl dichloride are placed in the apparatus described in Example 1. A total of 1340 g of dry chlorine is passed in at 160° C. within 9.5 hours under illumination. No interfering formation of a sublimate occurs during the chlorination.

After completion of chlorination, the reaction mixture is freed of dissolved chlorine and other gases by blowing in nitrogen. The reaction mixture is subsequently distilled under reduced pressure (12.0 to 13.3 mbar). 1193 g of a colourless mixture of terephthaloyl and isophthaloyl dichlorides are obtained. Boiling point 132°-137° C. degree of purity 99.9%.

Yield: 96.9% of theory.

EXAMPLE 4

The chlorination is carried out as described in Example 1, but the chlorination is discontinued prematurely at a content of 94.4% of terephthaloyl dichloride in the chlorination batch.

After removal of chlorine and other gases dissolved in the reaction mixture by passing in nitrogen, the reaction mixture is fractionally distilled under reduced pressure. 771 g of colourless terephthaloyl dichloride are obtained. Boiling point 140°-141° C./21 mbar; melting point 82° C.; degree of purity ≧99.9%. 426 g of a product results as tailings, which product contains 85.4% of terephthaloyl dichloride, 12.2% of terephthalate acid chloromethyl ester chloride, 0.7% of di-(chloromethyl) terephthalate and 1.7% of unknown compounds.

These tailings are mixed with 777 g (4 mols) of dimethyl terephthalate in the following batch and again subjected to the chlorination described in Example 1. Again, no formation of a sublimate is observed in the chlorination.

On distillation of this second batch, 784 g of terephthaloyl dichloride (degree of purity ≧99.9%) are obtained as the main run and 431 g of tailings containing terephthaloyl dichloride are obtained.

These tailings are again re-used in the next batch.

What is claimed is:

1. In a process for the preparation of terephthaloyl and/or isophthaloyl dichloride by chlorination of dimethyl terephthalate and/or dimethyl isophthalate with chlorine gas at a temperature from 100° to 250° C., the improvement wherein the process is carried out in the presence of 20 to 200% by weight, relative to the combined amount of dimethyl terephthalate and dimethyl isophthalate, of terephthaloyl and/or isophthaloyl dichloride.

2. A process according to claim 1, wherein said terephthaloyl and/or isophthaloyl dichloride is added to said dimethyl terephthalate and/or dimethyl isophthalate.

3. A process according to claim 2, wherein said terephthaloyl and/or isophthaloyl dichloride is added to a dimethyl isophthalate prior to a commencement of the reaction.

4. A process according to claim 1, wherein said terephthaloyl and/or isophthaloyl dichloride are brought in contact with said dimethyl terephthalate and/or dimethyl isophthalate prior to commencement of said chlorination.

5. A process according to claim 1, wherein said dimethyl terephthalate and/or dimethyl isophthalate are added to said terephthaloyl and/or isophthaloyl dichloride.

6. A process according to claim 1, wherein said terephthaloyl and/or isophthaloyl dichloride is recycled terephthaloyl and/or isophthaloyl dichloride obtained by chlorination of dimethyl terephthalate and/or dimethyl isophthalate with chlorine in the presence of terephthaloyl and/or isophthaloyl dichloride.

7. A process according to claim 1, wherein said terephthaloyl and/or isophthaloyl dichloride is added in an amount of 30 to 100% by weight relative to the combined weight of dimethyl terephthalate and dimethyl isophthalate.

8. A process according to claim 1, wherein the chlorination is discontinued when the content of terephthaloyl and/or isophthaloyl dichloride in the reaction mixture has risen to 90-98% by weight of the theoretically possible content.

9. A process according to claim 8, wherein the chlorination mixture is fractionally distilled and the tailings from the distillation which contain terephthaloyl and/or isophthaloyl dichloride are added to dimethyl terephthalate and/or dimethyl isophthalate feed for the chlorination.

10. A process according to claim 1, wherein the chlorination is effected in the absence of light.

11. A process according to claim 1, wherein the process is carried out in the presence of UV light.

12. A process according to claim 1, wherein the process is carried out in the presence of a catalyst which promotes side chain chlorination of aromatic compounds.

* * * * *

UNITED STATES PATENT AND TRADEMARK OFFICE
CERTIFICATE OF CORRECTION

PATENT NO. : 4,528,146
DATED : July 9, 1985
INVENTOR(S) : Walter Böckmann, et al It is certified that error appears in the above-identified patent and that said Letters Patent is hereby corrected as shown below:

Col. 5, line 2    Delete "a" and substitute --said--

Col. 5, line 3    Before "commencement" delete "a"

Signed and Sealed this

Fifteenth Day of October 1985

[SEAL]

Attest:

Attesting Officer

DONALD J. QUIGG

Commissioner of Patents and Trademarks—Designate